United States Patent
Marceaux et al.

(10) Patent No.: US 6,361,564 B1
(45) Date of Patent: Mar. 26, 2002

(54) TOTAL KNEE JOINT COMPRISING AN INSERT MOVABLE RELATIVE TO A TENON

(75) Inventors: Pascal Marceaux; Jean-François Biegun, both of Chaumont; Jean-Yves Jenny, Lipsheim, all of (FR); Rolf Miehlke, Munster (DE); Dominique Saragaglia, Claix (FR)

(73) Assignee: Aesculap (FR)

( * ) Notice: Subject to any disclaimer, the term of this patent is extended or adjusted under 35 U.S.C. 154(b) by 0 days.

(21) Appl. No.: 09/491,597

(22) Filed: Jan. 25, 2000

(30) Foreign Application Priority Data

Feb. 2, 1999 (FR) .............................. 99 01158
Jul. 5, 1999 (FR) .............................. 69 08632

(51) Int. Cl.[7] .................................................. A61F 2/38
(52) U.S. Cl. ................................ 623/20.29; 623/20.28
(58) Field of Search ........................ 623/22.14, 22.15, 623/22.17–22.28, 22.32, 22.36, 22.37, 22.4, 22.42

(56) References Cited

U.S. PATENT DOCUMENTS

| | | | |
|---|---|---|---|
| 5,395,401 A | * 3/1995 | Bahler | ............................ 623/20 |
| 5,609,639 A | 3/1997 | Walker | ........................ 623/20 |
| 5,702,466 A | * 12/1997 | Pappas et al. | ................. 623/20 |
| 5,755,801 A | * 5/1998 | Walker et al. | ................. 623/20 |
| 5,782,925 A | * 7/1998 | Collazo et al. | ................ 623/20 |
| 6,099,570 A | * 8/2000 | Livet et al. | ............... 623/20.01 |
| 6,162,254 A | * 12/2000 | Timoteo | .................. 623/20.33 |

* cited by examiner

Primary Examiner—Corrine McDermott
Assistant Examiner—Hieu Phan
(74) Attorney, Agent, or Firm—Renner, Kenner, Greive, Bobak, Taylor & Weber

(57) ABSTRACT

A knee-joint prosthesis including a tibial insert (5) between a tibial plate (1) provided on its outer surface with means for fixing to a tibia, and a femoral part comprising a condyle provided with means for fixing to the femur, the tibia insert (5) being mounted on the tibial plate (1) and comprising at least two upper surfaces (7) complementary in shape with the outer surface of the condyles, a tenon (2, 3, 4) is fixed to the inner surface of the tibial plate (1) and projects upwards and comprises an oblong part (4) extending parallel to the inner surface of the tibial plate (1), and the tibial insert (5) has a cavity (9) in which the oblong part (4) engages with possibility of rotation and translation of the tenon (2) relative to the tibial insert (5).

13 Claims, 4 Drawing Sheets

FIG. 3a
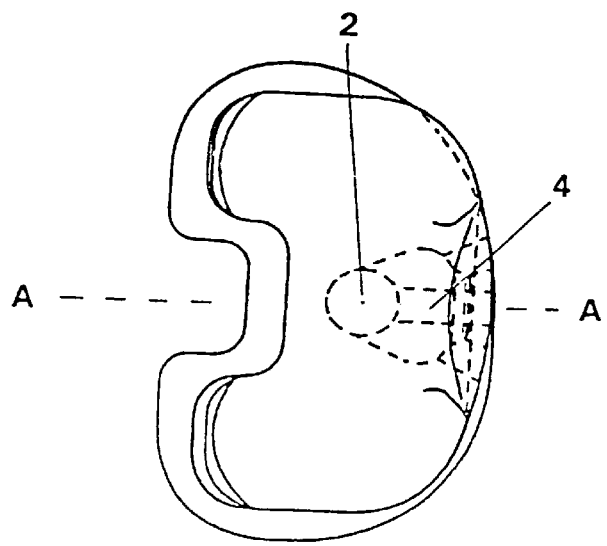
FIG. 3b
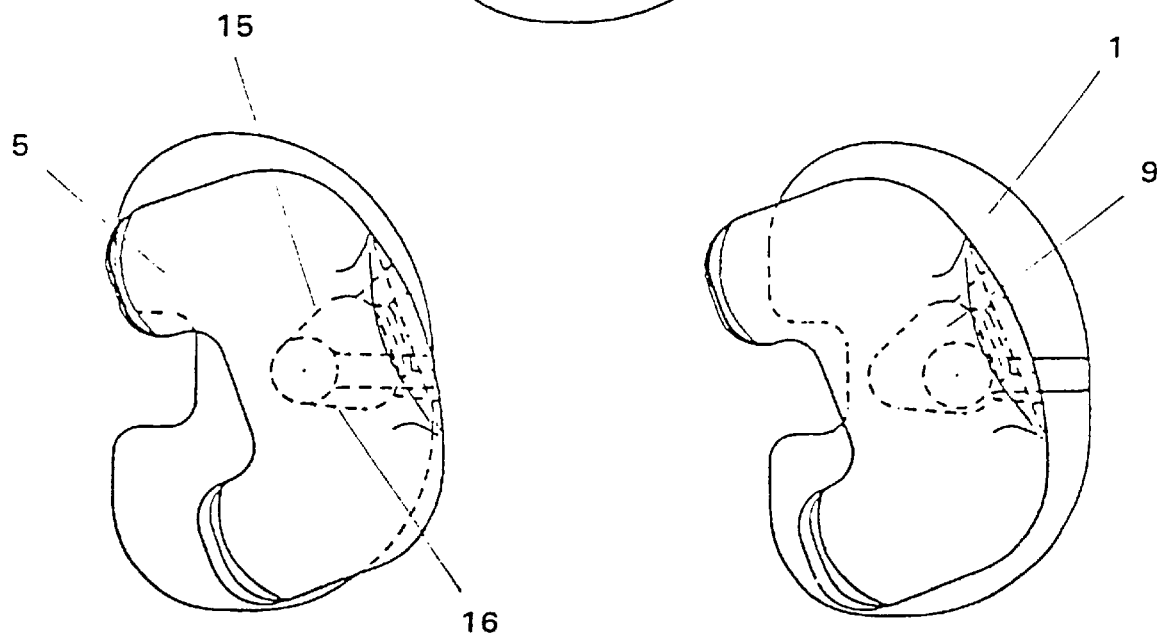
FIG. 3c
COUPE A-A
FIG. 4

TOTAL KNEE JOINT COMPRISING AN INSERT MOVABLE RELATIVE TO A TENON

The invention relates to a total knee-joint prosthesis comprising a tibial part, a femoral part and a tibial insert for joining the tibial part to the femoral part. The invention also relates to a tibial insert of this kind.

A similar total knee-joint prosthesis is already known from European Patent Application No: 92 113726.1 in the name of AESCULAP AG. According to this prior-art document, the total knee prosthesis is made up of a tibial part comprising a tibia plate fixed to the proximal part of the tibia by an anchoring rod anchored in the medullary cavity cc the tibia, a femoral part comprising two condyles fixed to the distal part of the femur, the condyles having spherical outer surfaces, and a tibial insert disposed on the tibial plate and on its upper part having surfaces complementary in shape with the surfaces of the condyles so that the condyles can slide relative to the tibial insert and so that the tibial part can bend relative to the femoral part. A means is provided for coupling the tibial insert to the tibial plate and comprises a journal mounted pivotably in a recess formed at the centre of the tibia plate, and an appendix which cooperates with a groove formed in the bottom part of the tibial insert so as to guide the tibial insert in translation and in rotation in the plane of the tibial plate relative to the said tibial plate.

This total knee prosthesis has the disadvantage that when the prosthesis is fitted, the practitioner must centre it perfectly in position so as exactly to correspond to the anatomy of the femur and the tibia. The slightest error in centring will make it necessary for the practitioner to start again.

The invention relates to a total knee prosthesis comprising a tibial insert between a tibial plate provided on its inner surface with means for anchoring to a proximal end of a tibia, and a femoral plate comprising condyles provided with means for anchoring to a distal part of a femur, the tibial insert being slidably mounted on the tibial plate and comprising upper surfaces complementary in shape with outer surfaces of the condyles, a tenon being mounted so as to project from the outer surface of the tibial plate and comprising a base and an oblong part extending from the base parallel to the outer surface of the tibial plate; and the tibial insert comprising a cavity in which the oblong part engages with possibility at least of rotation of the oblong part relative to the tibial part, characterised in that the size and shape of the cavity are such that the base of the tenon in the cavity can move relative to the tibial insert in antero-posterior and/or medio-lateral translation.

Thus, the prosthesis is centred dynamically by simple medio-lateral movement of the insert relative to the tibial plate when the prosthesis is fitted.

The prior-art total knee prosthesis have the further disadvantage that when the knee is bent, owing to uncontrolled movements, the journal may come loose from the bore in which it is mounted in the tibial plate, resulting in undesirable separation of the tibial insert and the femoral part from the tibial plate.

Also, rotation of the tibial part relative to the tibial plate is not limited, since the coupling means can make a complete rotation around the bore, which does not correspond to the rotation normally observed in the case of the anatomical knee.

According to an improvement of the invention, the tenon is fixed to the tibial plate.

Another reason for fixing the tenon to the tibial plate is to prevent the tenon coming loose from the bore formed in the tibial plate. In order however to allow the tibial insert to rotate relative to the tibial plate, a cavity is provided sufficient in size to permit rotation of the oblong part of the tenon in the cavity over a given range of rotation, e.g. ±25° or preferably ±15°.

In a preferred embodiment, the oblong part is at a distance on the tibial plate, the cavity comprises a first lateral opening formed in the anterior lateral wall of the tibial insert and a second rear opening, the lateral opening being of a size allowing the oblong part to move through it and the rear opening being bounded by bottom edges of the lateral walls of the cavity and by a bottom edge of the bottom rim defined by the lateral first opening of the abutment, so as to form a hole which limits the sliding motion in antero-posterior or medio-lateral translation of the base of the tenon relative to the tibial plate, and the bottom rim of the first opening forms an abutment which cooperates with the oblong part so as to prevent upward detachment of the tibial insert from the tibial plate.

The abutment is provided so as to prevent anterior luxation of the insert relative to the tibia if the posterior crossed ligament (PCL) is cut, since the abutment takes over the function of the PCL of limiting anterior movement when the knee bends.

The invention also relates to a tibial insert as used in the tibial knee prosthesis described hereinbefore.

We shall now by way of example describe an embodiment of a total knee prosthesis comprising a movable insert according to the invention, with reference to the drawings, given by way of example only and in which:

FIGS. 3A, 3B and 3C are top views showing the possible movements of the tibial insert relative to the tibial plate when the tibial insert has been assembled on the tibial plate;

FIG. 4 is a view in section along line A—A in FIG. 3A;

The embodiment described in FIGS. 5 to 8 is similar to that in FIGS. 1 to 4. Like elements or elements having a like function are indicated by the same reference numbers.

Figure 1:
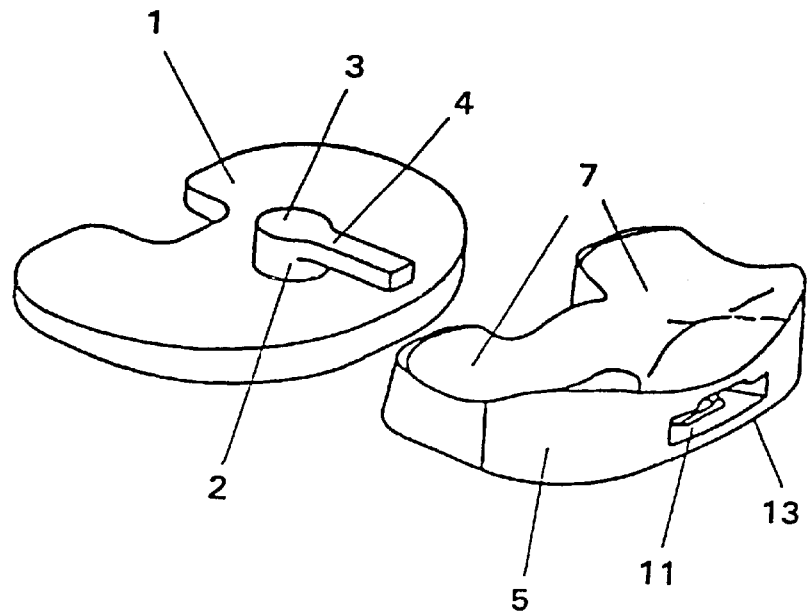
FIG. 1 is a perspective top view of the tibial insert and of a tibial plate according to the invention, in the non-assembled state.
Figure 2:
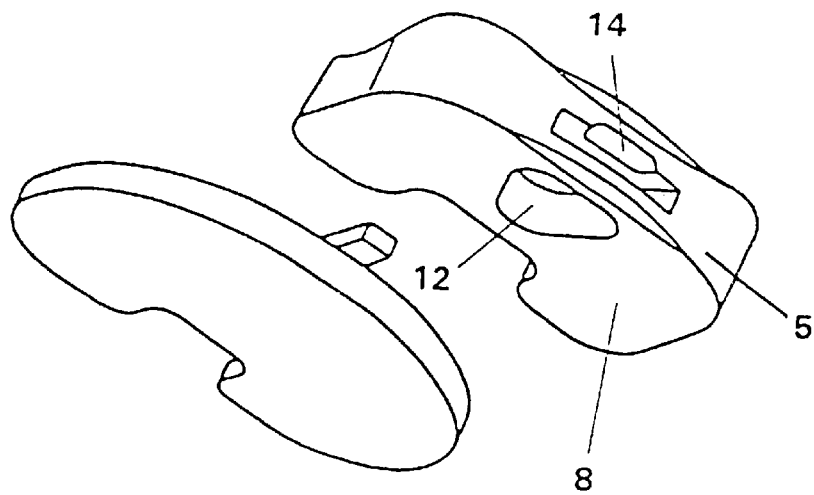
FIG. 2 is a perspective bottom view of he tibial insert and the tibial plate in FIG. 1.

FIG. 1 shows a tibial plate 1 for anchoring to the proximal end of a tibia (not shown) by an anchoring member (also not shown) disposed under the tibial plate. A tenon 2 projecting from the top part of the tibial plate 1 comprises a base 3 and a prolongation 4 in the form of a strip and having a rectangular cross-section. The base 3 of the s trip is fixed immovably and non-rotatably to the tibia plate 1, and the prolongation 4 is disposed so as to extend longitudinally in the antero-posterior direction (the antero-posterior direction being the direction from the knee hollow towards the front part of the knee where the knee projects). The right cross-section of the prolongation 4 is rectangular, but the shape could alternatively be circular, elliptical, square or otherwise. The prolongation 4 extends from the upper part of the base 3 of the tenon, at a distance e (1 mm to 10 mm) from the tibial plate.

In another possible embodiment of the invention, the prolongation 4 of the tenon 2 can be directly in contact with the a tibial plate 1, and can be without the abutment described hereinafter in the cavity of the tibial insert (see description hereinafter). This second possible embodiment also results in a number of advantages of the invention, i.e. limitation of dislocation by prevention of dislocation of he tenor 2 in the tibial plate, tolerance of medio-lateral movement and consequent good centring of the femur relative to the tibia, and limitatio n of rotation of the tibial insert relative to the tibial plate.

In the assembled st ate, the upper surface of the tibial plate 1 receives a tibial insert 5, the tibial insert 5 being made e.g. of polyethylene or similar material and having an upper base made up of two curved surfaces 7 with upward facing concavity and each adapted to receive a complementary curved surface of a respective one of two condyles (not shown) fixed to the distal end of the femur. The tibial insert 5 also comprises a flat bottom surface 8 adapted to rest on the tibial plate 1 and slide thereon when the total knee prosthesis is in the assembled position.

The tibial insert 5 has a cavity 9. The cavity 9 is formed in the bottom part of the tibial insert 5, in the anterior part. The cavity 9 is symmetrical with respect to the medio-lateral plane of the tibial insert, i.e. the plane containing the antero-posterior axis, i.e. the plane containing the antero-posterior axis and also the axis normal to the bottom surface of the tibial insert. The cavity 9 is bounded at the top by a top wall 10 and laterally by a first and a second lateral wall 15, 16 which include an angle of approximately 30° and join at the rear part of the tibial insert in a rounded shape corresponding to the rounded or circular shape of the lateral wall of the base 3 of tenon 2.

The cavity 9 also has a lateral first opening 11 and a rear second opening 12. The rear opening 12 is in the shape of an isosceles, inter alia equilateral, triangle with sides joining in rounded parts complementary in shape with the rounded part of the base 3 of the tenon 2. The first opening 11 is formed in the anterior lateral part of the tibial insert 5 and is sufficient in size to allow the prolongation 4 to move through it and to move in rotation from one to the other lateral wall 15, 16 of the cavity 9.

In the embodiment described here, an abutment 13 is provided between the two openings 11, 12 and comprises the anterior bottom edge of the tibial insert 5. When the total knee prosthesis is in the fitted position, the abutment is positioned above the tibial plane 1 under the prolongation 4 and thus prevents too easy detachment of he tibial insert from the tibial plane, or displacement of the tibial insert from the plate.

FIGS. 3A, 3B, 3C snow the movements of the tibial insert 5 relative to the tibial plate 1. In FIG. 3A, the tibial plate and the tibial insert are disposed parallel to one another, the cavity 9 being divided into two equal parts by the base 3 and the prolongation 4 of the tenon 2. The tibial insert can rotate relative to the tibial plate, the said movement in rotation being possible until the prolongation 4 abuts against the lateral wall 16 of the cavity. The result is a rotation of about +15° of the tibial insert relative to the tibial plate. Equivalent rotation in the other direction is also possible, so that the deflection of the tibial plate relative to the tibial insert is approximately ±15°. The limitation of the rotation of the insert relative to the tibial plate can be adjusted by modifying the angle between the lateral walls 15 and 16. The angle will usually be chosen between 30° and 50°, corresponding to limitation of mutual rotation between ±15° and ±25°. Also, movement in translation of the tenon along the antero-posterior axis of the knee is possible, as shown in FIG. 3C. This movement is limited by the abutment 13, against which the base 3 of the tenon 2 comes after the tibial insert travels to the rear relative to the tibial plate.

In the other direction (forward travel of the tibial insert relative to the tibial plate), the base 3 of the tenon 2 likewise abuts against the corner common to the two walls 15 and 16. This limitation of movement of the insert relative to the plate enables the knee prosthesis to be used whether the posterior crossed ligament (PCL) is retained or cut. In the latter case the antero-posterior movement is limited by the corner common to the two walls 15 and 16, taking over from the PCL and preventing luxation of the insert when the knee bends.

Also, as can be seen, medio-lateral movement of the tibial plate relative to the tibial insert is possible when the base 3 of tenon 2 moves along the lateral walls 15, 16 of the cavity or along the inner face of the abutment 13 or inside the domain defined by the said lateral walls and the said abutment 13. This results in dynamic compensation of the centring of the femoral part relative to the tibial part, which is sometimes difficult to obtain under static conditions when fitting the prosthesis.

In another possible embodiment of the invention, a cut-out 14 can be provided at the level of the top part of the lateral opening of the cavity 9, to facilitate insertion of the tenon 2 into the cavity 9 and through the opening 11 when the knee prosthesis is positioned.

Figure 5:
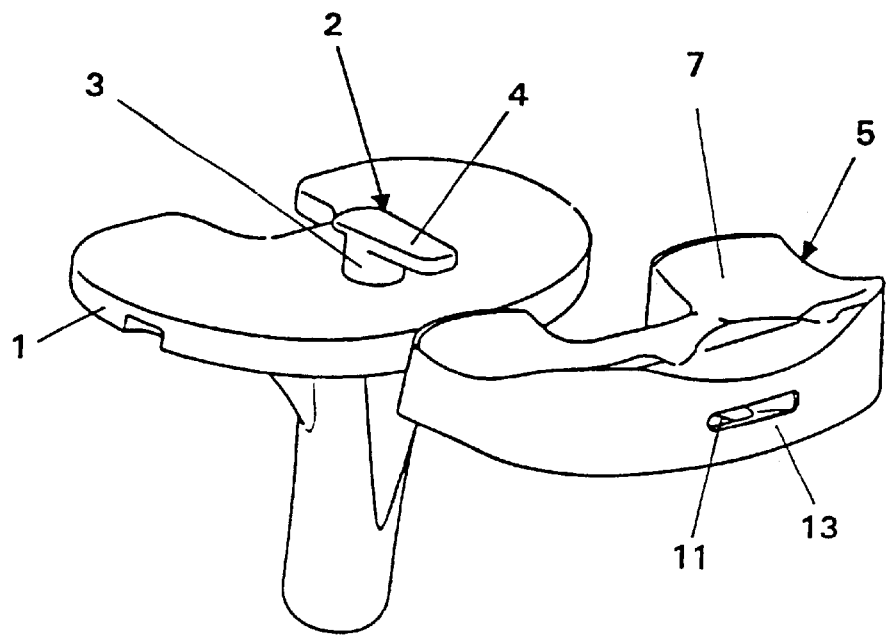
FIG. 5 is a perspective top view of the tibial insert and of a tibial plate in the non-assembled state and in a variant embodiment of the invention.
Figure 6:
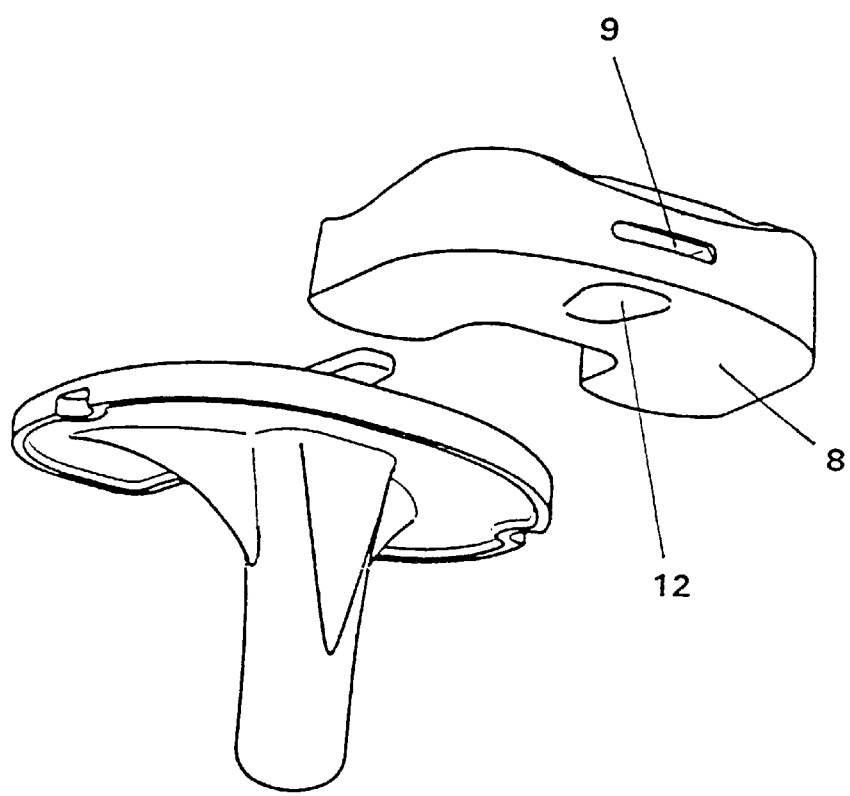
FIG. 6 is a perspective bottom view of the tibial insert and of the tibial plate in FIG. 5.
Figure 8:
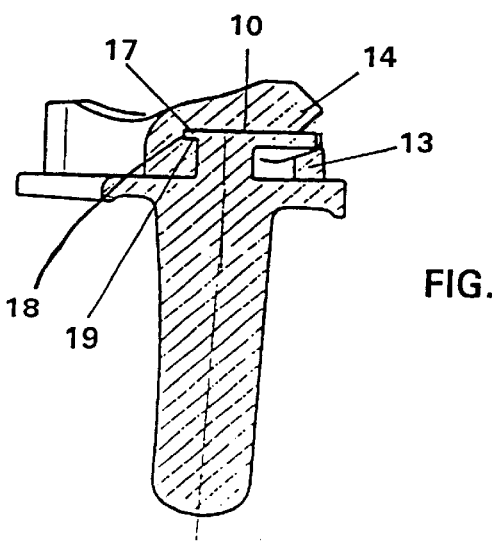
FIG. 8 is a view in section along A—A in FIG. 7A.

FIG. 5 shows a tibial plate 1 for anchoring to the proximal end of a tibia (not shown) by an anchoring member (also not shown) disposed under the tibial plate. A tenon 2 projecting from the top part of the tibial plate 1 comprises a base 3 and a prolongation 4 in the form of a bevelled strip and having a rectangular cross-section. The base 3 of the strip is fixed immovably and non-rotatably to the tibial plate 1, and the prolongation 4 is disposed so as to extend longitudinally in the antero-posterior direction (the antero-posterior direction being the direction from the knee hollow towards the front part of the knee where the knee projects). The right cross-section of the prolongation 4 is rectangular, but the shape could alternatively be circular, elliptical, square or otherwise. The prolongation 4 extends from the upper part of the base 3 of the tenon, at a distance (1 mm to 10 mm) from the tibial plate.

In another possible embodiment of the invention, the prolongation 4 of the tenon 2 can be directly in contact with the tibial plate 1, and can be without the abutment described hereinafter in the cavity of the tibial insert (see description hereinafter).

In the assembled state, the upper surface of the tibial plate 1 receives a tibial insert 5, the tibial insert 5 being made e.g. of polyethylene or similar material and having an upper base made up of two curved surfaces 7 with upward facing concavity and each adapted to receive a complementary curved surface of a respective one of two condyles (not shown) fixed to the distal end of the femur. The tibial insert 5 also comprises a flat bottom surface 8 adapted to rest on the tibial plate 1 and slide thereon when the total knee prosthesis is in the assembled position.

The tibial insert 5 has a cavity 9. The cavity 9 is formed in the bottom part of the tibial insert 5, in the anterior part. The cavity 9 is symmetrical with respect to the medial plane of the tibial insert, i.e. the plane containing the antero-posterior axis, i.e. the plane containing the antero-posterior axis and also the axis normal to the bottom surface of the tibial insert. The cavity 9 is bounded at the top by a top wall 10 and laterally by a first and a second lateral wall 15, 16 which include an angle of approximately 30° and join at the rear part of the tibial insert in a rounded shape corresponding to the rounded or circular shape of the lateral wall of the base 3 of tenon 2.

The cavity 9 also has a lateral first opening 11 and a rear second opening 12. The rear opening 12 is in the shape of an isosceles, inter alia equilateral, triangle with sides joining in rounded parts complementary in shape with the rounded part of the base 3 of the tenon 2. The first opening 11 is formed in the anterior lateral part of the tibial insert 5 and is sufficient in size to allow the prolongation 4 to move through it and to move in rotation from one to the other lateral wall 15, 16 of the cavity 9.

In the embodiment described here, a rim forming an abutment 13 is provided between the two openings 11, 12 and comprises the anterior bottom edge of the tibial insert 5. When the total knee prosthesis is in the fitted position, the abutment is positioned above the tibial plane 1 under the prolongation 4 and thus prevents too easy detachment of the tibial insert from the tibial plane, or displacement of the tibial insert from the plate.

Figure 7A:
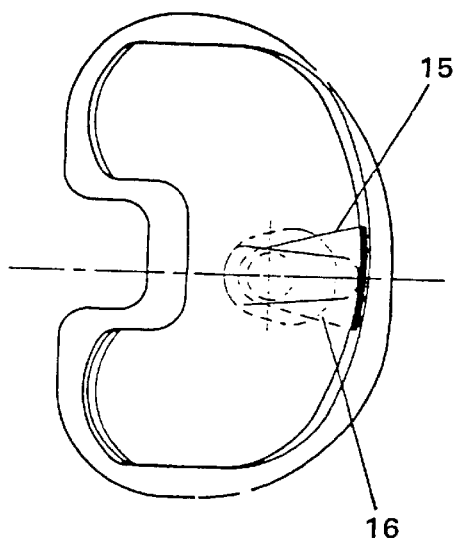
FIGS. 7A, 7B, 7C and 7D are top views showing the possible movements of the tibial insert relative to the tibial plate when the tibial insert is assembled on the tibial plate in FIGS. 5 and 6.
Figure 7B:
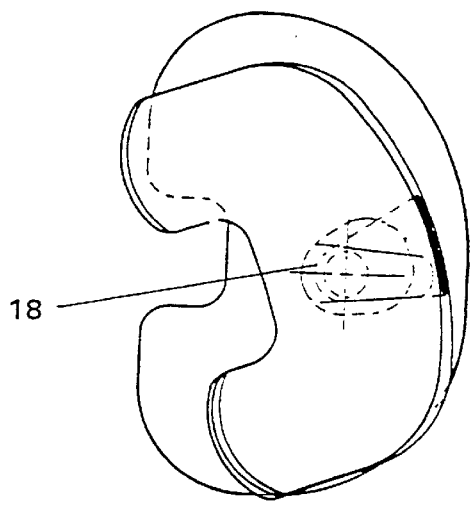
Figure 7C:
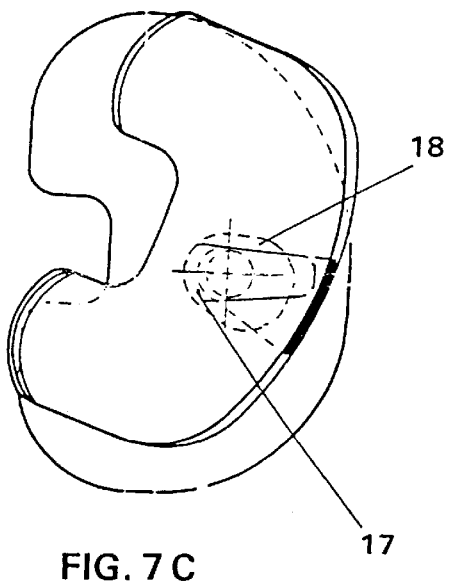
Figure 7D:
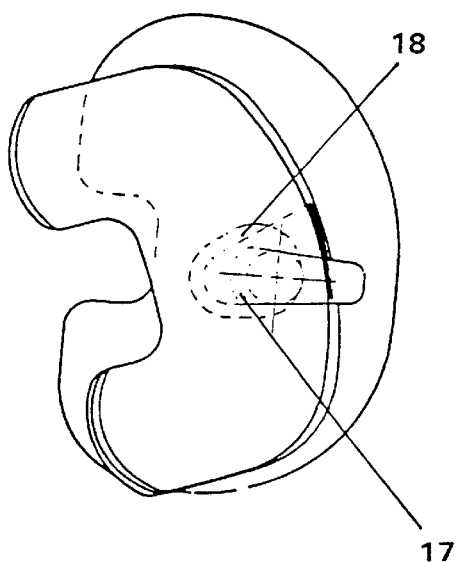

FIGS. 7A, 7B, 7C show the movements of the tibial insert 5 relative to the tibial plate 1. In FIG. 7A, the tibial plate and the tibial insert are disposed parallel to one another, the cavity 9 being divided into two equal parts by the base 3 and the prolongation 4 of the tenon 2. The tibial insert can rotate relative to the tibial plate, the said movement in rotation being possible until the prolongation 4 abuts against the lateral wall 16 of the cavity (FIG. 7B). The result is a rotation of about +15° of the tibial insert relative to the tibial plate. Equivalent rotation in the other direction is also possible (FIG. 7C), so that the deflection of the tibial plate relative to the tibial insert is approximately ±15°. The limitation of the rotation of the insert relative to the tibial plate can be adjusted by modifying the angle between the lateral walls 15 and 16. The angle will usually be chosen between 30° and 50°, corresponding to limitation of mutual rotation between ±15° and ±25°. Also, movement in translation of the tenon along the antero-posterior axis of the knee is possible, as shown in FIG. 7D. This movement is limited by the abutment 13, against which the base 3 of the tenon 2 comes after the tibial insert travels to the rear relative to the tibial plate.

In the other direction (forward travel of the tibial insert relative to the tibial plate), the base 3 of the tenon 2 likewise abuts against the corner common to the two walls 15 and 16. This limitation of movement of the insert relative to the plate enables he knee prosthesis to be used whether the posterior crossed ligament (PCL) is retained or cut. In the latter case the antero-posterior movement is limited by the corner common to the two walls 15 and 16, taking over from the PCL and preventing luxation of the insert when the knee bends.

Also, as can be seen, medio-lateral movement of the tibial plate relative to the tibial insert is possible when the base 3 of tenon 2 moves along the lateral walls 15, 16 of the cavity or along the inner face of the abutment 13 or inside the domain defined by the said lateral walls and the said abutment 13. This results in dynamic compensation of the centring of the femoral part relative to the tibial part, which is sometimes difficult to obtain under static conditions when fitting the prosthesis.

In another possible embodiment of the invention, a cut-out 14 can be provided at the level of the top part of the lateral opening of the cavity 9, to facilitate insertion of the tenon 2 into the cavity 9 and through the opening 11 when the knee prosthesis is positioned.

The oblong part 4 also projects in the other direction opposite to that in which it extends from the base 3, via a protuberance 17 in the shape of a half-disc. The protuberance 17 co-operates with a groove 18 formed in the cavity 9. In the medial plane, i.e. in the plane defined by the antero-posterior axis and the longitudinal axis of the tibia (normal o the plane of the tibial plate) the protuberance 17 is complementary in shape to the groove 18. This complementary in shape enables the protuberance 17 to be locked in the groove 18 by the bottom edge 19 of the groove 18, which serves as an abutment for the protuberance and prevents tilting relative to an axis perpendicular to the plane of symmetry in the left-right direction, i.e. prevents the insert 5 coming loose from the tibial plate 1. This anti-tilting effect can be provides alone, i.e. without providing the abutment 13 (e.g. as previously described when the prolongation 4 is directly in contact with the tibial plate), the purpose likewise being, in co-operation with the oblong part 4, to prevent the said tilting, or the effect may be combined with the abutment 13 to obtain a still greater anti-tilting effect inter alia in both directions, i.e. tilting of the insert relative to the tibial plate in the clockwise direction (abutment 19) in FIG. 4 or in the opposite direction (abutment 13).

The size of the groove 18 in the plane perpendicular to the plane of symmetry is greater than that of the abutment 13, so that when the tibial insert 5 rotates relative to the tenon 2, the abutment 13 slides in the groove 18 and does not interfere with the said reciprocal rotation.

The embodiment here describes a single protuberance disposed opposite the oblong part 4. Alternatively the protuberance 17 can be offset through an angle relative to the said antero-posterior direction, or a number of protuberances can be provided, e.g. two separated at an angle from one another and each co-operating with the groove 18.

A medio lateral translation is a translation in a direction perpendicular to the medial plane.

What we claim is:

1. A total knee prosthesis comprising a tibial insert between a tibial plate provided on its inner surface with means for anchoring to a proximal end of a tibia, the tibial insert being slidably mounted on the tibial plate,
   a tenon being mounted so as to project from the outer surface of the tibial plate and comprising a base and an oblong part extending from the base parallel to the outer surface of the tibial plate; and
   the tibial insert comprising a cavity in which the oblong part engages with possibility at least of rotation of the oblong part relative to the tibial insert, wherein the size and shape of the cavity are such that the base of the tenon in the cavity can move relative to the tibial insert in any antero-posterior and/or medio-lateral translation in said cavity.

2. A total knee-joint prosthesis according to claim 1, wherein the tenon is mounted fixed on the tibial plate.

3. A total knee-joint prosthesis according to claim 2, wherein an auxiliary projection is provided from the base of the tenon and can be inserted into an auxiliary recess in the cavity, the recess being complementary in shape with the protuberance, the bottom edge of the recess forming a second abutment which co-operates with the auxiliary projection so as to prevent the insert from tilting.

4. A total knee-joint prosthesis according to claim 3, wherein the auxiliary projection co-operates with the second abutment to prevent the insert tilting from the rear of the knee toward the front thereof.

5. A total knee-joint prosthesis according to claim 4, wherein the projection is in the form of a circular half-ring extending from the top of the base and the auxiliary recess comprises a groove formed in the upper part of the cavity and dimensioned along the walls of the cavity sufficiently so as not to block rotation of the oblong part relative to the tibial insert.

6. A total knee-joint prosthesis according to claim 4, wherein the projection proceeds from the oblong part and extends in the opposite direction to the oblong part.

7. A total knee-joint prosthesis according to claim 1, wherein the oblong part is at a distance from the tibial plate, the cavity comprises a first lateral opening formed in an anterior lateral wall of the tibial insert and a second rear opening, the lateral opening being of a size allowing the oblong part to move through it and the rear opening being bounded by bottom edges of the lateral walls of the cavity and by the bottom edge of the bottom rim of the lateral first opening, so as to form a hole which limits the sliding motion in antero-posterior or medio-lateral translation of the base of the tenon relative to the tibial plate and the bottom rim of the first opening forms an abutment which co-operates with the oblong part so as to prevent upward detachment.

8. A total knee-joint prosthesis according to claim 7, wherein the hole is in the shape of an isosceles triangle having corners complementary in shape with the lateral wall of the base of the tenon.

9. A total knee-joint prosthesis according to claim 8, wherein the angle of the isosceles triangle is between 30° to 50°.

10. A total knee-joint prosthesis according to claim 1, wherein the surface of a lateral wall of the base is circular.

11. A total knee-joint prosthesis according to claim 1, wherein two lateral walls of the cavity extend from a corner formed at their mutual intersection to the anterior side of the knee, the corner angle formed between them being between 30° and 50°.

12. A total knee prosthesis comprising a tibial insert between a tibial plate provided on its inner surface with means for anchoring to a proximal end of a tibia, the tibial insert being slidably mounted on the tibial plate and comprising a tenon being mounted so as to project from the outer surface of the tibial plate and comprising a base and an oblong part extending from the base parallel to the outer surface of the tibial plate; and the tibial insert comprising a cavity in which the oblong part engages with possibility at least of rotation of the oblong part relative to the tibial insert, wherein the size and shape of the cavity are such that the base of the tenon in the cavity can move relative to the tibial insert in antero-posterior and/or medio-lateral translation in said cavity, wherein the hole is in the shape of an isosceles triangle having corners complementary in shape with the lateral wall of the base of the tenon.

13. A total knee-joint prosthesis according to claim 12, wherein the angle of the isosceles triangle is between 30° and 50°.

* * * * *